United States Patent [19]
Zaks et al.

[11] Patent Number: 5,935,828
[45] Date of Patent: Aug. 10, 1999

[54] ENZYMATIC PRODUCTION OF MONOGLYCERIDES CONTAINING OMEGA-3 UNSATURATED FATTY ACIDS

[75] Inventors: Aleksey Zaks, Brookline; Akiva T. Gross, Newton, both of Mass.

[73] Assignee: Opta Food Ingredients, Inc., Bedford, Mass.

[21] Appl. No.: 07/345,622

[22] Filed: May 1, 1989

[51] Int. Cl.$^6$ .................................. C12P 7/64; C12P 7/62
[52] U.S. Cl. ........................................ 435/134; 435/135
[58] Field of Search ...................... 435/134, 135

[56] References Cited

U.S. PATENT DOCUMENTS

| | | | |
|---|---|---|---|
| 4,607,652 | 8/1986 | Mendy et al. | 514/547 |
| 4,792,418 | 12/1988 | Rubin et al. | 260/412 |

FOREIGN PATENT DOCUMENTS

| | | | |
|---|---|---|---|
| 2000143 | 4/1990 | Canada | 435/134 |
| 0274798 | 7/1988 | European Pat. Off. | |
| 2617501 | 6/1989 | France | 435/134 |
| 60-78587 | 5/1985 | Japan | 435/134 |
| 1-215286 | 8/1989 | Japan | 435/134 |
| 1-215490 | 9/1989 | Japan | 435/134 |
| 2188057 | 9/1987 | United Kingdom | 435/134 |

OTHER PUBLICATIONS

Chemical Abstracts, vol. 105, No. 5, p. 610 (1986) Abstract No. 41278b.
Chemical Abstracts, vol. 105, No. 5, p. 610 (1986) Abstract No. 41279c.
Chemical Abstracts, vol. 104, No. 17, p. 550 (1986) Abstract No. 147186q.
Chemical Abstracts, vol. 104, No. 23 p. 605 (1986) Abstract No. 205559b.
G.G. Haraldsson et al., *Tetrahedron Letters*, 30:1671–1674 (1989).
Zaks, A. and A. Klibanov, *Science 224:*1249 (1984).
Malcata et al., *JAOCS* 67:890–910 (1990).
Hills et al., *JAOCS* 67:561–564 (1990).
Baumann et al., *Angew. Chem. Int. Engl.* 27:41–62 (1988).
JP HEI 1[1989]–225490, filed Mar. 7, 1988 Applicant: Amano Pharmaceuticals K.K.
Macrae, Biotechnology for the Oils and Fats Industry, Ratledge et al. (Eds.), Am. Oil. Chem. Soc., Champaign, IL 1984, pp. 189–198.
I.L. Gatfield, *Annals of the New York Academy of Science*, 434: 569–572 (1984).
M.M. Hoq et al., *Argic. Biol. Chem.,* 49(2):335–342 (1985).
M.M. Hoq et al., *Journal of the American Oil Chemists' Society,* 61(4):776–781 (1984).
Y. Tsujisaka et al., *Biochim. Biophys. Acta,* 489(3):415–422 (1977).
R.A. Wisdom et al., *Enzyme Microb. Technol.,* 6(10):443–446 (1984).
F. Bozoglu et al., *J. Agric. Food. Chem.,* 32:2–6 (1984).
R.G. Jensen et al., *Journal of the American Oil Chemists' Society,* 55:422–427 (1978).
N.O.V. Sonntag, *Journal of the American Oil Chemists' Society,* 56:751A–754A (1979).
Abstract: M.K. Tahoun et al., *Microbios. Lett.,* 28(111–112).
Abstract: R. Bacaloglu et al., *Rev. Roum. Biochim,* 22(3): 177–181 (1985).
Abstract: N. Muthukumaran and S.C. Dhar, *Leather Science,* 30(3):97–100 (1983).
Abstract: T. Funada et al., *Nippon Kagaku Kaishi,* 12:1797–1805 (1983).
Abstract: German patent 3,447,024, D. Wullbrandt, et al. (1986).
Abstract: Japanese patent 50/49489, Tsujisaka et al. (1975).
Abstract: M. Pina and J. Graille, *Bull. Tech./Gattefosse Rep,* 76:34–36 (1983).
Yongmanitchai et al. (1989) 24(4), 117–124, *Process Biochem.*
Pavin et al. (1982) "Introduction to Organic Laboratory Techniques a Contemporary Approach", 2nd Ed., pp. 482–484, W.B. Saunders, New York.
Markley (1964) in "Techniques of Separation, Part 3, A: Distillation Salt Solubility, Low Temperature Crystallization", pp. 2081–2123, Interscience Publishers.
Lazar et al. (1985) in "World Conference of Emerging Techol, Fats Oils Ind." pp. 346–354.
Borzotröm (1964) *Biochim Biophys Acta.,* 84, pp. 228–230.
Shoichi et al. (1988) Chem Abstract. No. 109:5280V, p. 508.

*Primary Examiner*—Jon P. Weber
*Attorney, Agent, or Firm*—Hamilton,Brook,Smith & Reynolds, P.C.

[57] ABSTRACT

An enzymatic process for preparing an oil based product significantly enriched in omega-3 fatty acids is disclosed. The process is a two-step procedure involving lipase-catalyzed transesterification of triglycerides followed by low-temperature crystallization. The process yields a mixture of highly pure monoglycerides, at least sixty-percent of which contain omega-3 fatty acids. The process can also be used to produce omega-3 enriched triglyceride products.

11 Claims, No Drawings

ENZYMATIC PRODUCTION OF MONOGLYCERIDES CONTAINING OMEGA-3 UNSATURATED FATTY ACIDS

BACKGROUND

Omega-3 fatty acids are long-chain polyunsaturated fatty acids synthesized by marine microalgae and accumulated in the form of lipids by higher marine organisms such as fish. Since Dyerberg and Bang (*Acta Med Scand,* (1976) 200:69–73) established the relationship between dietary marine fish consumption and reduced incidence of coronary heart disease, numerous studies have confirmed several specific effects of a diet high in polyunsaturated fatty acids. Among these are the reduction of triglyceride levels in blood (Sanders, T. A. B. et al., *Arteriosclerosis,* (1985) 5:880–5), and reduction of low density and very low density lipoproteins (Illinworth, D. R. et al., *Arteriosclerosis,* (1984) 4:270–5). Furthermore, cancer studies show that omega-3 fatty acids may help to decrease the incidence, growth, and metastatic spread of tumors Karmali R. A. et al., *JNCI,* (1984) 73:457–461.

Since it has been shown that the consumption of omega-3 fatty acids from fish has a beneficial effect in reducing the incidence of coronary heart disease, alternative sources of omega-3 fatty acids have been sought to provide these benefits where consuming large amounts of fish is not desirable or practical. One of these sources is marine microalgae, which produce significant quantities of omega-3 fatty acid. It has been reported that some species of marine microalgae have an omega-3 fatty acids content ten fold higher than fish oils on a dry weight basis. Kyle, D. et al., *World Conference on Biotechnology for the Fats and Oils Industry,* (1988) p. 117–22.

Another method for providing higher levels of omega-3 fatty acids without consuming large amounts of fish oils is upgrading. There are several methods for upgrading fish oils which result in their enrichment with omega-3 fatty acids. For example, oils which have a high content of saturated fatty acids can be "winterized" by slow cooling to about 5° C. The major drawback of "winterization" is insignificant enrichment (about 10%) of omega-3 fatty acids.

Another technique is molecular distillation. The process takes place at high temperatures and low vacuum (of the order of $10^{-6}$ mm Hg). This process is highly energy consuming and results in a significant distraction of labile highly unsaturated fatty acids.

Other methods, which require the use of organic solvents, include crystallization, chromatography and supercritical carbon dioxide extraction. These processes have a number of drawbacks. For example, crystallization typically results in only small omega-3 enrichment of the product, and chromatography and supercritical fluid extraction are expensive and difficult to scale up.

Another approach for concentration of omega-3 fatty acids is based on chemical hydrolysis (or esterification) of fish oils, which is followed by a complex purification.

An alternative approach for enrichment of omega-3 fatty acids is based on lipase-catalyzed enzymatic refinement of fish oils. For example, Japanese patent 134446, June 29, 1984, to Kao Corp., describes a process which utilizes a lipase, *Arthrobacter urefaciens,* which is specific for saturated fatty acids, for the hydrolysis of fish oils. A similar process which is based on the natural preference of some lipases for saturated fatty acid moieties is described in Japanese patent 134446, Jul. 16, 1982, to Nippon Oils and Fats Co.

A different approach, which results in the production of triglycerides enriched in omega-3 fatty acids, is based on a two step enzymatic process. Japan Patent 234,588, Nov. 21, 1985, to Asahi Denka Kogyo Co.

There are several limitations to the enzymatic processes described above. These include the necessity for a complex separation of the product from free saturated fatty acids, which are the by-products of the hydrolysis reaction, and use of complex multienzymic systems and low efficiency that results in an insufficient degree of upgrading. An efficient cost-effective method of enriching the level of omega-3 fatty acids is needed.

SUMMARY OF THE INVENTION

The invention relates to an enzymatic process for preparing an oil-based product significantly enriched in omega-3 fatty acids compared to natural marine oils. The technique is based on a two-step process: lipase-catalyzed transesterification of triglycerides in an alcohol medium which is followed by low temperature crystallization. As a result of the present procedure, monoglycerides containing 60% (by volume) and higher of omega-3 fatty acids are obtained.

In the present process, a suitable fish oil is added to an alcohol containing a certain amount of water. A selected lipase is then added to the reaction medium and a suspension is formed (enzymes are insoluble in most organic solvents). After the reaction is completed, the enzyme is removed and monoglycerides enriched in omega-3 fatty acids are separated. They are then dissolved in an appropriate organic solvent, and subjected to low temperature crystallization, which causes selective crystallization of the monoglycerides containing predominantly saturated monoglycerides. The crystals are removed, and the solvent, which contains the omega-3 enriched monoglyceride product, is evaporated. As a result of the process, highly pure monoglycerides which are significantly enriched in omega-3 fatty acids are obtained.

In another embodiment of the present process, omega-3 enriched triglycerides are produced by the further step of lipase-catalyzed esterification, or transesterification, of the enriched monoglycerides. In this step, the enriched monoglycerides are esterified with selected fatty acids, or transesterified with fatty acid esters, in a non-aqueous medium (e.g. hexane or ethyl ether). After the reaction is completed, the enzyme is isolated by centrifugation, the solvent is evaporated and the product is purified by chromatography or distillation. The process yields nutritionally valuable triglycerides containing an omega-3 fatty acid moiety in the 2-position, and the selected fatty acids in the 1- and 3-positions. Diglycerides can also be produced in this way, that is, by esterification of fatty acids or transesterification of fatty acid esters with the enriched monoglyceride.

The present process yields natural food ingredients which are derived directly from fish oil and are significantly enriched in omega-3 fatty acids compared to the natural fish oil. Its chemical composition makes it superior to other commercially available products, since most of those containing similar concentrations of omega-3 fatty acids are based on esters of fatty acids. Other advantages of the present process include mild reaction conditions, high operational stability of the catalyst, no need for catalyst immobilization, easy product separation, and high degree of omega-3 enrichment.

DETAILED DESCRIPTION OF THE INVENTION

The unique properties of fish or marine oils which provide significant health benefits are attributed primarily to two polyunsaturated fatty acids: eicosapentaenoic acid (EPA), which has a 20 carbon chain and docosahexaenoic acid (DHA), which has a 22 carbon chain.

The invention is a two-step process: lipase-catalyzed transesterification of triglycerides in an alcohol medium, followed by low-temperature crystallization. The first step utilizes the ability of a selected lipase, suspended in an alcohol medium containing a small amount of water, to catalyze the partial transesterification of triglycerides to form monoglycerides acylated in the 2-position, in high yield. Since EPA and DHA occur naturally predominantly in the 2-position of triglycerides the present process provides monoglycerides significantly enriched in EPA and DHA.

As a result of the transesterification reaction, 2-monoacylated glycerides can be isolated in a 90%, or greater, yield. The high yield of the product in the process is based in part on the discovery that the specificity of some lipases towards the $C_1$ and $C_3$ positions of triglycerides is enhanced by using a non-aqueous reaction medium, such as alcohol. Moreover, due to the low water activity in 95–98% ethanol, chemical acyl migration is markedly suppressed, compared to that in aqueous solutions. In addition, lipases are much more stable in 95–98% ethanol than in aqueous solutions.

A suspension of the enzyme in ethanol, for example, containing the triglyceride catalyzes the formation of the ethyl ester of the fatty acids derived from the $C_1$ and $C_3$ positions of the triglyceride. The major products of the transesterification reaction, therefore, are ethyl esters of the fatty acids from the $C_1$ and $C_3$ positions and a monoglyceride acylated at the $C_2$ position. Since the chemical composition of marine oils is such that omega-3 fatty acids, such as EPA and DHA, are attached predominantly to the 2-position of triglycerides, the removal of the saturated fatty acids from the $C_1$ and $C_3$ positions results in monoglycerides significantly enriched in EPA and DHA.

The transesterification reaction produces a mixture of 2-monoglycerides: the desired product containing omega-3-fatty acids, and by-products which are monoglycerides acylated with saturated fatty acids (e.g., palmitic and stearic acids). The difference in solubility of the products of interest and these by-products is utilized in the second step of the present process for further enrichment of monoglycerides with omega-3 fatty acids. Unsaturated monoglycerides (i.e., monoglycerides with omega-3 fatty acids) are soluble in some organic solvents, such as hexane, acetone and tetrahydrofuran, at low temperatures such as −20° C., whereas saturated monoglycerides are practically insoluble in the same solvents at these temperatures. Saturated monoglycerides crystallize, or precipitate, from the solution and can be easily removed by filtration. Removal of the undesirable saturated products yields a concentrated solution of unsaturated monoglycerides containing at least 60% EPA and DHA. The solvent is removed by evaporation leaving a highly pure, 2-monoglyceride product rich in omega-3 fatty acids.

A wide variety of sources of triglycerides having omega-3 fatty acids, such as marine oils, can be used as the starting product in the present process. Omega-3 fatty acids are a class of fatty acids characterized by a double bond in the hydrocarbon chain, located between the 3rd and the 4th carbon atoms from the distal, or non-carboyxlate end of the fatty acid chain (i.e., the ω-carbon). Oils derived from various fish contain omega-3 fatty acids, for example, oils such as Atlantic cod, mackerel, menhaden, salmon, trout, etc. contain about 10% or more of EPA and DHA, are particularly useful sources.

Lipases derived from a variety of sources, including mammals, yeast, mold and bacteria can be employed. Lipases used in the present process should exhibit high operational stability (e.g., loss of no more than 50% activity after 50 hours of operation), be active in a non-aqueous organic media (e.g., having a water content of about 10% or less), and efficiently catalyze the transesterification reaction between an alcohol and a triglyceride. Lipases derived from *Pseudomonas fluorescens* and porcine pancreas, for example, satisfy these requirements. In the present process, lipase derived from *Pseudomonas fluorescens* retained at least 80% its original activity after continuous use for at least 72 hours.

The enzymatic reaction is carried out in an alcohol medium with the alcohol also serving as one of the reactants. Various primary aliphatic alcohols containing from about one to about eight carbon atoms, and mixtures thereof, can be used, including, for example, methanol, ethanol, propanol, isopropanol, butanol, isobutanol, pentanol, pentanediol, isopentanol, hexanol, and octanol. Ethanol is a particularly useful alcohol in the present process.

The water concentration in the reaction medium is of primary importance. A small amount of water is needed in order to activate the enzyme. Depending on the hydrophobicity of the reaction medium, this amount of water can vary from about 1 to about 7% (v/v). The more hydrophobic the alcohol, the less water is needed. As used herein, the term "more hydrophobic" means an alcohol with a longer carbon chain. If ethanol is used as a reaction medium, for example, 3–5% (v/v) water is optimal. It should be understood that up to a certain point, the rate of the reaction is proportional to the water concentration in the reaction medium. However, the use of higher concentrations of water (e.g., >10%) is not recommended, as it can have several negative effects, including decreasing the solubility of the oils in the reaction medium, destabilizing the enzyme, adversely affecting the specificity of the enzyme, complicating purification and promoting an undesirable hydrolysis reaction.

The term "water" is meant to include water-based solutions, such as buffers, which can also be used in the process. In Example 1, for example, HEPES buffer was used.

The first step of the process of the present invention is described in detail in co-pending U.S. patent application U.S. Ser. No. 07/253,110 filed Oct. 4, 1988, the teachings of which are incorporated herein by reference. Briefly, an oil containing omega-$^3$ fatty acids, such as fish oil, is added to the reaction vessel containing the alcohol and a small amount of water. The reaction is started by the addition of lipase to the reaction medium. The enzyme can be in the form of a dry powder or immobilized on a support, such as diatomaceous earth or Amberlite. After the addition of enzyme, the reaction mixture is agitated by stirring with an impeller, or by shaking. The agitation speed should be sufficient to form and maintain the suspension. The reaction mixture is maintained at a temperature in the range from about 20 to about 60° C., until most of the oil is converted to monoglycerides. Depending on the concentration of enzyme in the reaction mixture and its activity, the amount of water and the reaction temperature, the reaction time can vary from about 5 to about 20 hrs. Optimal conditions for a given set of reaction parameters can be determined empirically. The course of the reaction can be monitored by following the formation of monoglycerides and the disappearance of di- and triglycerides using gas chromatography. It is essential that the degree of conversion is such that the concentration of diglycerides in the reaction mixture does not exceed about 10% by weight of the concentration of monoglycerides. The presence of higher concentrations of diglycerides adversely affects the next step of the process, i.e., purification of the unsaturated 2-monoglycerides by low temperature crystallization.

After the desired degree of conversion from triglycerides to monoglycerides is achieved, e.g., greater than or equal to 90%, the reaction is stopped by removing the enzyme, for example, by centrifugation or filtration. The monoglyceride products are then separated from the free fatty acids and fatty acid esters by membrane filtration or chromatography.

In the second step of the process, the monoglycerides are then dissolved in an appropriate solvent, which can be any solvent capable of dissolving the reaction products, and having a higher affinity for unsaturated monoglycerides than for saturated monoglycerides, so that at low temperatures, the monoglycerides containing saturated fatty acids will preferentially crystallize, leaving the unsaturated monoglycerides in solution. Hexane, acetone and tetrahydrofuran are particularly useful solvents for this purpose. The solution is then incubated at about −20 to −25° C. for several hours. Pellets of the saturated monoglycerides, formed as a result of the low-temperature crystallization, are then separated from the mother-liquor, by filtration or centrifugation, for example. Solvent is evaporated from the remaining supernatant under vacuum, leaving behind a mixture of pure, unsaturated monoglycerides enriched in omega-3 fatty acids.

In another embodiment of the present invention, omega-3 enriched triglycerides can be produced by the further step of lipase-catalyzed esterification (if fatty acids are used) or transesterification (if fatty acid esters are used) of the enriched monoglycerides. In this third step of the process, the monoglycerides are contacted with a lipase catalyst and with selected fatty acids, or fatty acid esters, in a non-aqueous medium. The non-aqueous medium can be any organic solvent containing less than 10% (by volume) water in which lipases are stable and active, and which does not have a detrimental effect on lipases, (e.g., DMSO or DMF both deleteriously affect lipases). Hexane is a particularly useful medium. The reaction is carried out substantially as described above for the first step of the reaction. After the reaction is completed, the enzyme is isolated by centrifugation or other appropriate method, and the solvent and water (which is formed as a by-product of esterification) are removed, for example, by evaporation. This step yields nutritionally valuable triglycerides containing an omega-3 fatty acid moiety in the 2-position. Short chain fatty acids or fatty acid esters (e.g., $C_2$–$C_5$), and medium chain fatty acids or esters (e.g., $C_6$–$C_{12}$) are useful for this step, as are certain long chain fatty acids (e.g., $C_{12}$ or higher) which have been shown to have some health-related beneficial effects, such as $C_{18}$linolenic acid.

The invention is further illustrated by the following specific exemplification.

EXEMPLIFICATION

Materials

Lipases (EC 3.1.1.3) were obtained from the following suppliers: porcine pancreatic lipase (1.1 IU/mg solid) from Sigma Chemical Co. (St. Louis, Mo.) and *Pseudomonas fluorescens* (30 IU/mg solid) from Amano International Enzyme Co. (Troy, Va.). Menhaden oil was generously provided by Zapata Heynie Corp. (Reedville, Va.). Silica gel (150 A, mesh size 35–75 μm) was purchased from Analtech (Newark, Del.). Boron trifluoride solution in methanol (14%), mixed tocopherols, EPA, DHA and their esters were obtained from Sigma Chemical Co. All solvents used in this work were of analytical grade and were obtained from Aldrich Chemical Co. (Milwaukee, Wis.).

Methods

Lipase Assays The activity of the lipases in the hydrolysis reaction was determined potentiometrically using radiometer RTS-812 recording pH-stat system with olive oil as a substrate. In a typical experiment 10 mL of an 0.02–0.1 g/mL aqueous solution of the substrate was placed in the cuvette of a pH-stat, and the pH was adjusted to 7.0. Lipase was then added, and the acid liberated as the result of the hydrolysis was automatically titrated with 0.5 M NaOH.

All products of enzymatic conversions were assayed by gas chromatography (Hewlett Packard 5890A) using 12-m fused silica capillary column (S.G.E. Australia). Nitrogen was used as a carrier gas (5 mL/min). Detector and injector port temperature were 350° C. Prior to injections, the samples were modified with hexamethyldisilazane following the standard procedure (Sweely et al., 1963, *J. Am. Chem. Soc.*, 85:2495–2507).

In addition to gas chromatography, the course of the reaction and purity of all products were analyzed by thin-layer chromatography (TLC) using Whatman K6 silica gel sheets. A mixture of petroleum ether (b.p. 30–60° C.), ether and acetic acid in a ratio of 90:10:1 was used as an eluting buffer. The spots were developed by spraying with 50% sulfuric acid, followed by 10 min heating at 180° C.

Fatty Acid Analysis

The analysis of fish oils and monoglycerides was performed following the standard procedure of Eining (Eining, *JAOCS*, 1987, 64:499–502) with slight modifications. A sample of material containing approximately 5 mg of EPA and 5 mg of DHA was dissolved in 1 mL of methylene chloride containing 0.01% of mixed tocopherols. One mL of 0.5 N solution of sodium hydroxide in methanol (containing the same amount of tocopherols) was added and the mixture was incubated at 40° C. for 50 min. One mL of a 14% solution of boron trifluoride in methanol was added and the mixture was incubated at 40° C. for another 50 min. After cooling, two mL of methylene chloride was added to the reaction medium and 2 μL samples were withdrawn and analyzed for EPA and DHA content by gas chromatography.

Separation

Separation of the reaction mixture was achieved by flash silica gel chromatography. After the completion of the reaction and removal of the enzyme, solvent was evaporated under reduced pressure. Reaction products (20 g) were applied on the column containing 100 g of silica gel equilibrated with a mixture of ether/petroleum ether (4:6). The by-products were eluted with 1 L of the above mixture at a flow rate of about 100 mL/min under water pump suction. Monoglycerides were then eluted in the same manner using anhydrous ether (600 mL). The solvent was evaporated under the reduced pressure yielding pure monoglycerides.

Further enrichment of the product with omega-3 fatty acids was achieved by a low-temperature crystallization from hexane. Monoglycerides obtained during the first step were dissolved in hexane at room temperature. The solution was incubated at −20° C. overnight. Crystals formed, containing predominantly saturated monoglycerides, which were then removed by centrifugation at −18° C. The solvent was evaporated under reduced pressure yielding pure monoglycerides.

EXAMPLE 1

Twenty mL of menhaden oil containing 22% (v/v) of EPA and DHA were placed in a round-bottom flask containing 180 mL of 95% (v/v) ethanol and 5% (v/v) of 50 mM HEPES buffer, (pH 7.6). The reaction was started by the addition of one gram of *Pseudomonas fluorescens* lipase in the form of dry powder. The suspension which formed was agitated on an orbit shaker at 250 rpm at 40° C. for 20 hours. The course of the reaction was monitored by gas chromatography following the disappearance of the starting material and the appearance of monoglycerides. After 20 hours, no starting material could be detected and the concentration of diglycerides did not exceed 5% of that of monoglycerides. The reaction was stopped by removing the enzyme by centrifugation. Ethanol was evaporated under vacuum using a rotary evaporator, and the monoglyceride product was purified by silica gel chromatography as described in "Methods". After purification, 5.3 g of 97% pure monoglycerides containing at least 40% EPA and DHA, were obtained.

Further purification of the monoglycerides was achieved by crystallization of the saturated monoglycerides from hexane. Monoglycerides (5.3 g) were dissolved in 35 mL hexane at room temperature. The solution was chilled to −20° C. and incubated at this temperature for 10 hours. The precipitate was removed by centrifugation at −20° C. Hexane was evaporated from the supernatant to yield 3.8 g of monoglycerides containing greater than 60% of EPA and DHA.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

We claim:

1. A process for producing omega-3 unsaturated fatty acid enriched 2-monoglycerides, comprising the steps of:

a) combining an alcohol medium (ethanol), a triglyceride which is a marine oil containing omega-3 unsaturated fatty acids, a lipase catalyst and an amount of water sufficient to activate the lipase, under conditions sufficient for transesterification to occur between the alcohol and the fatty acids located on the 1- and 3-positions of the triglyceride, thereby producing 2-monoglycerides containing omega-3 fatty acids;

b) contacting the monoglycerides obtained in (a) with an organic solvent to preferentially dissolve unsaturated monoglycerides therein and reducing the temperature of the solution of monoglycerides to precipitate monoglycerides containing saturated fatty acids, thereby leaving a supernatant containing 2-monoglycerides having omega-3 unsaturated fatty acids that is substantially free of saturated monoglycerides;

c) separating the precipitate obtained in (b) from the supernatant, and d) removing the solvent from the supernatant to obtain 2-monoglycerides enriched in omega-3 unsaturated fatty acids compared to natural marine oils.

2. The process of claim 1, wherein the triglyceride is a fish oil which contains omega-3 unsaturated fatty acids.

3. The process of claim 2, wherein the fish oil is menhaden oil.

4. The process of claim 1, wherein the omega-3 unsaturated fatty acids are selected from the group consisting of eicosapentaenoic acid, docosahexaenoic acid and mixtures thereof.

5. The process of claim 1, wherein said lipase is derived from *Pseudomonas fluorescens* or porcine pancrease.

6. The process of claim 5, wherein the lipase is immobilized.

7. The process of claim 1, wherein the amount of water is from about 1 to about 7 percent by volume.

8. The process of claim 1, wherein the organic solvent is hexane.

9. The process of claim 1, wherein step (b) is performed by low temperature crystallization.

10. The process of claim 1, wherein the alcohol in said alcohol medium is selected from the group consisting of methanol, ethanol, propanol, butanol, isobutanol, pentanol, pentanediol, isopentanol, hexanol, octanol and mixtures thereof.

11. The process of claim 10, wherein the alcohol medium is ethanol.

\* \* \* \* \*